(12) United States Patent
Li et al.

(10) Patent No.: US 11,555,215 B2
(45) Date of Patent: *Jan. 17, 2023

(54) ELECTROSPUN FIBERS FOR PROTEIN STABILIZATION AND STORAGE

(71) Applicant: GLOBAL LIFE SCIENCES SOLUTIONS OPERATIONS UK LTD, Sheffield (GB)

(72) Inventors: Bing Li, Clifton Park, NY (US); David Roger Moore, Rexford, NY (US); William Christopher Alberts, Saratoga Springs, NY (US); John Richard Nelson, Clifton Park, NY (US)

(73) Assignee: GLOBAL LIFE SCIENCES SOLUTIONS OPERATIONS UK LTD, Sheffield (GB)

( * ) Notice: Subject to any disclaimer, the term of this patent is extended or adjusted under 35 U.S.C. 154(b) by 453 days.

This patent is subject to a terminal disclaimer.

(21) Appl. No.: 16/261,532

(22) Filed: Jan. 29, 2019

(65) Prior Publication Data

US 2019/0153517 A1    May 23, 2019

Related U.S. Application Data

(62) Division of application No. 14/140,127, filed on Dec. 24, 2013, now Pat. No. 10,202,636.

(51) Int. Cl.
*C12Q 1/6806* (2018.01)
*G01N 33/543* (2006.01)

(52) U.S. Cl.
CPC ..... *C12Q 1/6806* (2013.01); *G01N 33/54346* (2013.01); *G01N 33/54393* (2013.01)

(58) Field of Classification Search
CPC .......... C12Q 1/6806; G01N 33/54346; G01N 33/54393
See application file for complete search history.

(56) References Cited

U.S. PATENT DOCUMENTS

| | | | |
|---|---|---|---|
| 10,202,636 B2 * | 2/2019 | Li | G01N 33/54393 |
| 2006/0094015 A1 * | 5/2006 | Smith | C12Q 1/6806 435/6.11 |
| 2009/0075354 A1 * | 3/2009 | Reneker | D04H 1/407 435/182 |
| 2009/0136932 A1 * | 5/2009 | Craighead | C12Q 1/6874 435/6.12 |

FOREIGN PATENT DOCUMENTS

WO    WO-2007144389 A2 * 12/2007 ......... A61L 27/3804

* cited by examiner

*Primary Examiner* — Jezia Riley
(74) *Attorney, Agent, or Firm* — Grogan, Tuccillo & Vanderleeden, LLP

(57) ABSTRACT

An electrospinning approach is disclosed for generating a dissolvable formulation of a reagent of interest in a nanoscale fiber medium. In one embodiment, the nanoscale fibers can incorporate and stabilize biological agents of interest, such as for storage at room temperature for extended periods. In one implementation, the fibers can be produced in a continuous manner and dissolve rapidly.

23 Claims, 4 Drawing Sheets

ELECTROSPUN FIBERS FOR PROTEIN STABILIZATION AND STORAGE

BACKGROUND

Figure 1:
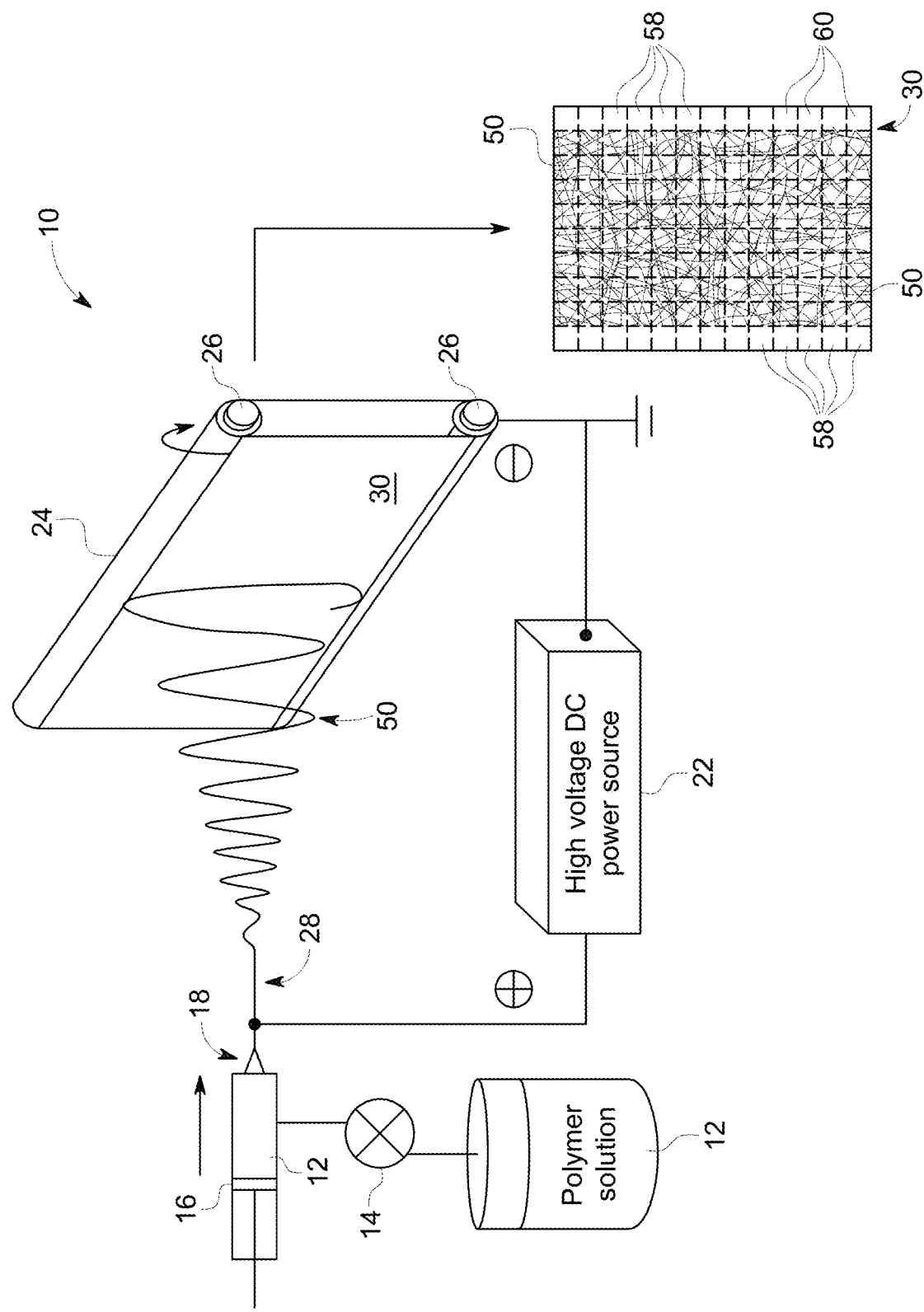
Figure 2:
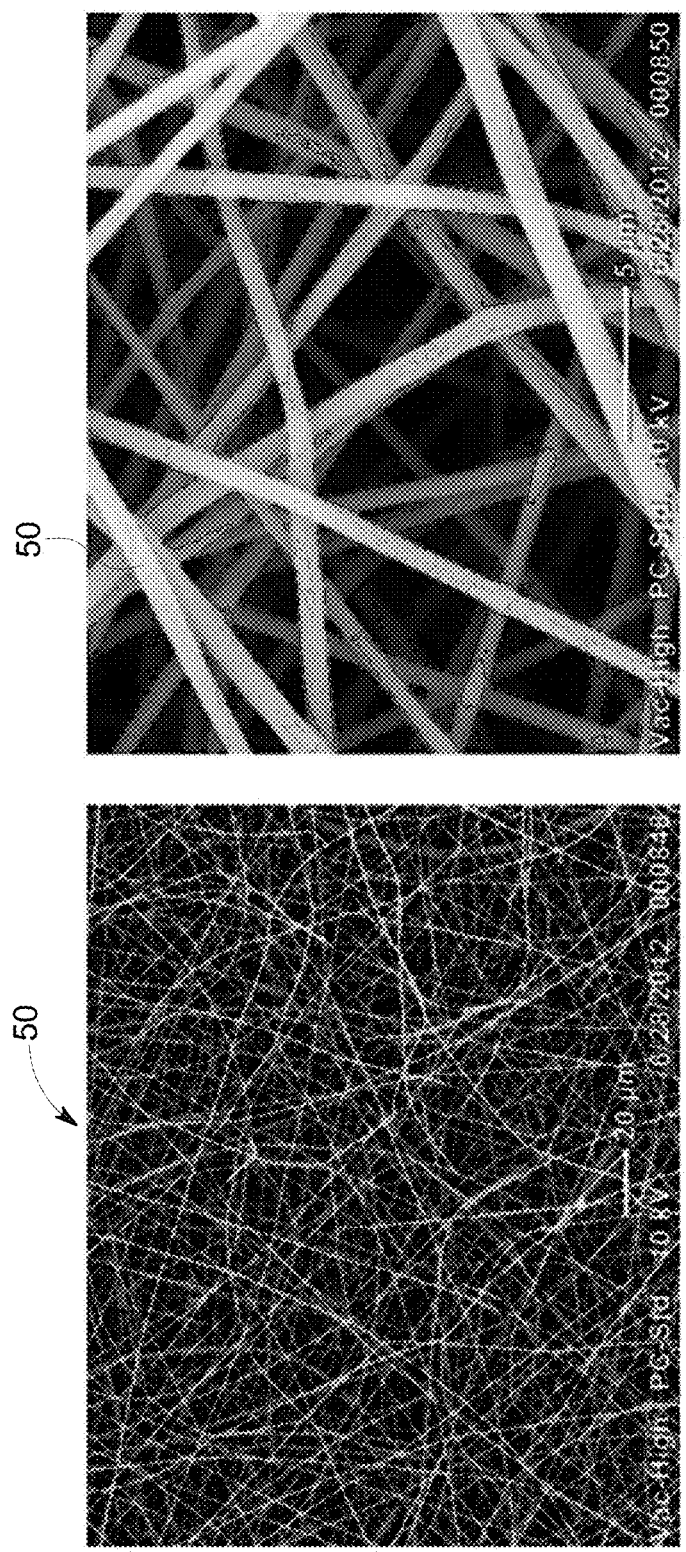
Figure 3:
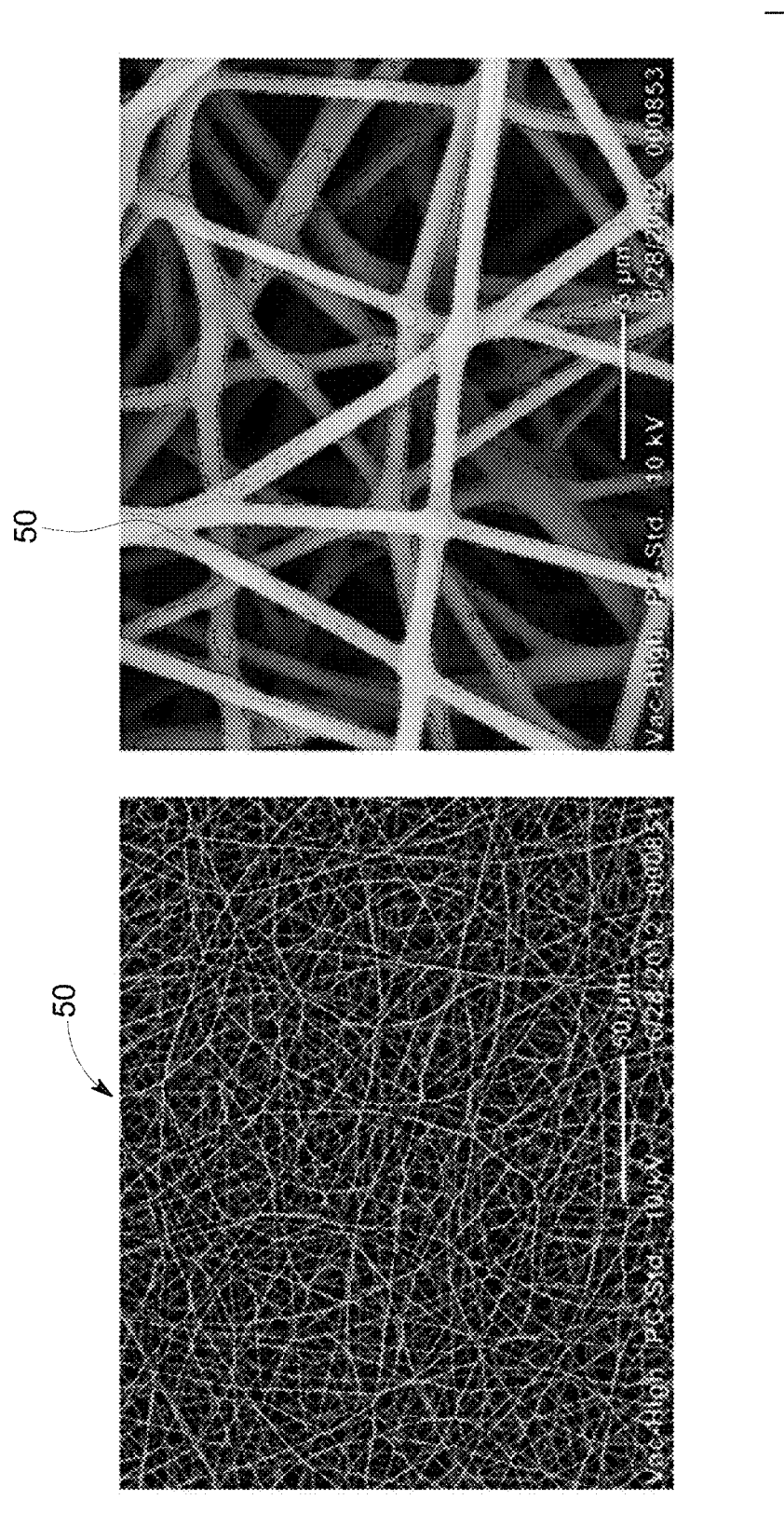
Figure 4:
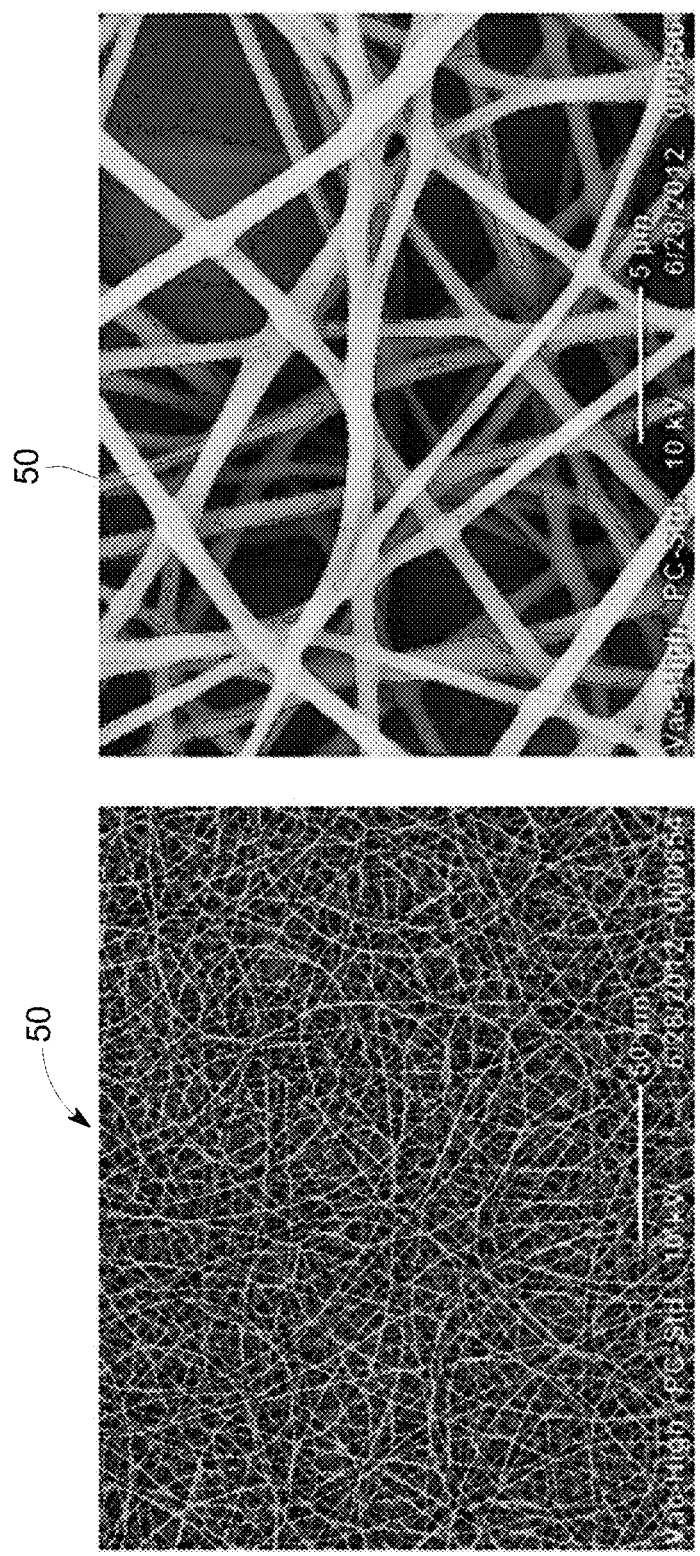

The subject matter disclosed herein generally relates to storage of materials and reagents used in biological and chemical processes.

Biologically active materials may be used in a variety of laboratory and analytic contexts. However, in general, such biologically active materials may have a relatively short shelf life if not treated or prepared to enhance their storage characteristics.

For example, various approaches for biological reagent stabilization and storage are known. One such approach includes storing the protein in a liquid format at reduced temperature (e.g., −20° C. to 8° C.). For instance, certain biological reagents may be stored in a 50% glycerol solution maintained at 4° C. or as low as −20° C. Alternatively, certain biological reagents may instead be frozen for storage, such as at or below −20° C. Obviously both of these storage approaches require refrigeration to maintain the biological activity of the reagent for extended time.

In addition, biological reagents may be stored in a lyophilized form, in which the reagent is dried by freezing in a high vacuum. Such lyophilized reagents may be stored at low temperature or at room temperature. However, the processes used to produce the lyophilized product may be complex and time consuming. In particular, certain such processes used to produce lyophilized cakes, films, beads or spheres of biological enzymatic mixtures that may be batch processes, that do not allow for continuous production of the product. In some methods, frozen solutions are dehydrated, requiring a complicated freeze drying method. Further, in such techniques the desired manufacturing tolerances, such as with respect to bead size, may be difficult to obtain or maintain.

BRIEF DESCRIPTION

In one embodiment, a biochemical storage medium is disclosed. The biochemical storage medium comprises one or more fibers. The one or more fibers have a nanoscale to microscale diameter and comprise one or more biologically active components.

In a further embodiment, a method of stabilizing a biologically active composition is disclosed. The method includes the act of feeding a solution comprising one or more biological molecules of interest to an extrusion component. The solution is expelled from the extrusion component. An electrostatic charge is applied to the expelled solution while applying an opposing charge to a collector surface. One or more fibers formed from the expelled and charged solution are collected on the collector surface. This method can be a non-batch process. The fibers have diameters measuring in nanometers to micrometers.

In an additional embodiment, a method of using a stabilized biologically active constituent is disclosed. The method includes the act of selecting a quantity of an electrospun fiber. The electrospun fibers have diameters between about 10 nm and about 2000 nm. The fibers comprise the stabilized biologically active constituent. The fibers have a very high surface to volume ratio. The fibers are added to an aqueous environment. The fibers dissolve in the aqueous environment to form an aqueous solution. The aqueous solution is used in a biological reaction in which the stabilized biologically active constituent takes part in the biological reaction.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 1 depicts an example of an electrospinning system suitable for generating stabilized fibers of a biological material, in accordance with aspects of the present disclosure;

FIG. 2 is a scanning electron micrograph of a stabilized fiber generated using an aqueous solution of 70% Ficoll® PM400 using a first set of parameters for the system of FIG. 1;

FIG. 3 is a scanning electron micrograph of a nanoscale fiber generated using an aqueous solution of 70% Ficoll® PM400 using a second set of parameters for the system of FIG. 1; and FIG. 4 is a scanning electron micrograph of a nanoscale fiber generated using an aqueous solution of 70% Ficoll® PM400 using a third set of parameters for the system of FIG. 1.

DETAILED DESCRIPTION

The present approaches relate to the preservation of biological samples and reagents (such as enzymes, antibodies, growth factors, and so forth) using an electrospinning approach suitable for generating nanoscale fibers comprising the biological reagent of interest as well as any added compositions or preservatives.

As used herein, a biochemical storage medium is a format for storage of protein reagents in an active state. The conditions for storage vary depending on the format of the medium. Conventionally, biological reagents, such as proteins, are stored at low temperature to preserve the stability and function of the reagent. Alternatively, room temperature storage of proteins or other biological agents may be possible using certain existing approaches that generate a lyophilized product. A room temperature formulation may include both the protein of interest as well as one or more stabilizing factors. Examples of protein stabilizing factors that may be included in such formulations include, but are not limited to, formulations of polysucrose (e.g., Ficoll® PM70, Ficoll® PM400 (which may include from 70 to 400 polymerized sucrose units) as well as other polymers composed of any number of repeated sucrose units), melezitose, trehalose, sucrose, sorbitol bovine serum albumin, polyethylene glycol, and polyvinyl alcohol.

In one such conventional approach, this combination of protein and stabilizing factors may undergo a freezing step in liquid nitrogen followed by a drying step, i.e., a freeze drying process, which allows the formulation to be stored at room temperature in a lyophilized form. For example, in one conventional approach droplets (e.g., 20 μl droplets) of an enzymatic mixture may be dropped into liquid nitrogen in a batch-type process. As part of the batch processing, when a certain number of droplets or volume of the mixture has been dropped into the liquid nitrogen, a filtration and vacuuming process may be subsequently performed to collect the product of this batch process, e.g., lyophilized beads of the desired enzymatic mixture. The lyophilized composition may be subsequently rehydrated prior to or during use. By way of example, such a process may be used to allow room temperature storage of enzymes used in nucleic acid amplification in a ready-to-go form, that allows a technician to add the desired enzymatic formulation to a reaction, or a system that automatically implements a desired reaction, as needed.

However, as will be, appreciated, such processes may be undesirably complex in terms of the number and types of steps that are performed. Further, in terms of production, such batch-type processes may also be undesirable due to the time consuming nature of the processes as well as other limitations that are attributable to batch-processing.

In contrast to these approaches, and as discussed herein, the present approach may be used to preserve proteins or other biological reagents without a freeze drying step and without being limited to batch processing. Instead, the present approach employs an electrospinning process to generate a dissolvable formulation of the reagent of interest in the nanoscale to microscale fiber format that can encapsulate proteins (or other suitable biological reagents) and stabilize the protein at room temperature for storage. Advantages of this process include, but are not limited to, a highly uniform fiber diameter of the electrospun product that dissolves when placed in water, such as dissolving in less than 10 minutes, less than 1 minute, less than 10 seconds, or less than 2 seconds, depending on the embodiment. In particular, the extensive surface area associated with the thin fibers allow very rapid dissolution of the fibers in a buffer, such as an aqueous buffer, though an organic solution may still be employed in certain implementations. Within the fiber are stabilized proteins (or other biologically reagents), which are released upon dissolution of the fiber with their biological activity intact. The electrospinning process can also be performed in a continuous manner, i.e., not in a batch process, and utilizes a primarily aqueous solution, as opposed organic solvents.

As discussed herein, electrospinning is an approach that utilizes an electrical charge in the generation of very fine fibers (e.g., microscale or nanoscale) from a liquid composition or solution. Because the electrospinning process does not require high temperatures, the process may be particularly suitable for producing fibers incorporating complex or large molecules, such as proteins or other molecules that may be found in biological samples or reagents.

Electrospinning, in general, utilizes a voltage to charge a portion of a liquid medium (e.g., a drop or droplet) such that the generated electrostatic forces overcome the surface tension associated with the liquid medium, stretching out the liquid medium to form a fine stream. In particular, beyond a threshold point, an electrostatically charged stream of the liquid medium is drawn from the surface of the liquid. The stream of liquid dries in flight, allowing the electrostatic charge to migrate to the surface of the liquid stream. In response to this charge migration, portions of the jet may electrostatically repel one another (such as at bends or twists in the stream) which acts to elongate the stream as these portions repel one another in a whipping or undulating motion (hence the "spinning" aspect of electrospinning). This self-repulsion and elongation of the stream may continue until the resulting dried fiber is deposited as a layer on a collector, which acts to ground any residual electrostatic charge.

The resulting fibers are substantially uniform in size and thickness and, in certain embodiments, have nanometer scale diameters (e.g., diameters between about 10 nm and about 2000 nm), i.e., nanofibers. As used herein, fibers produced by this method that have diameters measuring in the nanometer to micrometer scale are referred to as nanoscale fibers. The dimensions, including diameter, of such fibers may be determined by a variety of factors, including the needle gauge and flow rate of the device (discussed below), the nature of the receiving substrate or collector, the charge density employed, and the travel distance of the stream to the collector, the electric field strength, as well as the composition of the liquid mixture or solution and the properties of the liquid mixture or solution. For example, properties of the composition of the liquid mixture or solution that may determine fiber dimensions include molecular weights of the included molecules, presence of a solvent or co-solvent, and/or concentration of the respective constituents. Similarly, properties of the liquid solution or mixture, such as the viscosity, surface tension, conductivity, and volatility, may determine fiber dimensions.

As discussed herein the present approach involves the stabilization of biologically active molecules into nanoscale fibers using electrospinning. Once stabilized as nanoscale fibers, the biologically active molecules may be stored at room temperature, e.g., between 50 CF to 90° F., such as 70° F. By way of example, in one study, antibodies electrospun into nanoscale fibers, as discussed herein, retained biological activity for over 30 days (e.g., 34 days) at room temperature. With this in mind, examples of suitable biologically active molecules, or mixtures of such molecules, for the present electrospinning approach include but are not limited to: enzymatic mixtures (including polymerases) and antibodies, sugars (e.g., melezitose, polysucrose, sucrose, polyethylene glycol, sorbitol, and so forth), nucleotides or strands of such nucleotides, and so forth. In addition, in certain implementations, constituents of the liquid polymer 12 may include, but are not limited to: labile small molecules, dNTP's, rNTP's, stabilizing factors (e.g., albumin, polyethylene glycol, polyvinyl alcohol, starch, sugar), detergents, salts, divalent cations, buffer molecules, primers, flavin adenine dinucleotide (FAD), nicotinamide adenine dinucleotide (NAD), dye conjugated esters, labeled molecules, and so forth.

With the preceding in mind, and turning to FIG. 1, an example of an electrospinning system 10 suitable for use with the present approach is disclosed. In the depicted example, a polymer solution 12 (such as an aqueous polymer solution) of one or more biological molecules of interest (such as a protein or proteins) is provided in an accessible container or vessel. A pump 14 may be employed to feed the polymer solution 12 to a syringe 16 or other suitable device capable of extruding or expelling the polymer solution at a suitable rate. In the depicted syringe 16 example, the polymer solution 12 may be expelled from a needle 18 or tip at a fixed rate.

In the depicted example, a high voltage (e.g., 5 kV to 50 kV) DC power source 22 is also provided. The power source 22 acts to electrostatically charge the polymer solution 12 as it is expelled from the syringe tip 18 and to oppositely charge the surface of the collector 24 on which the nanoscale fibers 50 will ultimately be deposited. In the depicted example, the collector 24 is grounded and, further, has a surface that may be continuously translated or otherwise moved, such as via one or more rotating cylinders 26, to facilitate continuous collection of the deposited nanoscale fibers 50 on the surface. In particular, in one embodiment, the collector 24 may be a continuously fed roll of substrate material 30, that may serve as a continuous deposition surface on which the nanoscale fibers 50 are deposited and collected for subsequent use. Examples of suitable substrate materials for fiber collection include, but are not limited to:

hydrophilic surfaces, hydrophobic surfaces, amphiphilic surfaces, a nitrocellulose membrane, a cellulose membrane, a cellulose acetate membrane, a regenerated cellulose membrane, a nitrocellulose mixed ester membrane, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane a glass fiber substrate, and/or any combination of two or more of the above membranes. In some embodiments the fibers are collected in a vessel for use, whereas in other embodiments the fibers are further processed into smaller pieces for use.

The liquid polymer in response to the applied electrostatic forces initially erupts from the tip 18 of the syringe 16 as a charged stream 28. As the stream 28 dries in flight, the electrostatic charge migrates to the surface of the stream 28. As this happens, the type of current flow associated with the stream 28, which is initially ohmic current flow, transitions to a convective current flow. As this transition occurs, the stream 28 may elongate and undulate, as discussed above, in response to repulsive forces caused by the surface charge where the stream 28 bends or twists, ultimately giving rise to the desired fiber 50 as the stream 28 transitions from a liquid to the solid fiber 50 as the associated liquid evaporates. As discussed herein the fiber 50 may have nanoscale dimensions and is collected on the collector 24, here a continuously fed roll or sheet of substrate material 30. As will be appreciated, the fibers 30 may be deposited in a uniform manner over the collection substrate 30 or may be deposited in a non-uniform manner, such as at particular locations on the collection substrate or with periodic breaks in the deposited layer of fibers 50 to allow the substrate to be separated at planned intervals as part of the production process.

The substrate 30 may be periodically collected with the electrospun fibers 50 (formed of the one or more biological molecules of interest) deposited on the surface of the substrate 30. In the depicted example, the substrate 30 having the fibers 50 on the surface may be processed (e.g., cut, sliced, stamped, and so forth)) into smaller, fiber-coated pieces 58 (e.g., squares or circles), denoted by dashed lines 60, suitable for shipping and/or storage, such as at room temperature. For example, based on the deposition thickness of the fibers 50, pieces 58 may be sized and cut so as to correspond to a dose or use of the fibers 50 formed of the one or more biologically active molecules of interest. Alternatively, the fibers 50 may be removed from the substrate 30 for packaging or storage apart from the substrate 30. For example, the fibers 50 may be removed from all or part of a substrate 30 after deposition. The removed fibers 50 may then be portioned out by mass or volume into a bulk storage container (e.g., a non-reactive container, such as a glass vial or jar) or into single- or multi-use packaging, such as blister or clamshell packaging where each blister corresponds to the amount of fibers 50 used in a single reaction of a given type.

For example, sufficient fibers 50 formed from a polymerase mixture may be provided in a packaging or storage container or may be provided on a piece 58 of substrate and may be added to or used to form a reaction mixture for a single PCR (or other nucleic acid amplification) operation. Thus, in practice, as user performing a nucleic acid amplification, might add a pre-measured amount of fibers 50, either alone or on a pre-cut piece 58 of substrate 30 to an aqueous solution or existing reaction solution. The fibers 50 rapidly dissolve (e.g., in two seconds or less) to join or form the solution, which could then be used in the desired amplification operation in conjunction with the sample to be amplified.

Applications that may benefit from such a novel storage format (i.e., electrospun nanoscale fibers) for biological materials include, but are not limited to, nucleic acid amplification operations (e.g., conventional, isothermal, genomic, and so forth) and immunoassay operations (e.g., lateral flow assays, enzyme linked immunosorbant assays, western blot assays, and so forth) for which enzymes, antibodies, or other protein mixtures may be added over the course of the operation. By way of example, an enzymatic mixture suitable for use in a polymerase chain reaction (PCR) system may be stabilized for room temperature storage using the electrospinning approach and fiber-based storage discussed herein. In this example, a sample of the electrospun fibers may be added, along with water and a DNA sample, to the system to facilitate implementation of such a reaction. Similarly, a suitable enzymatic or antibody mixture for use in various types of assay or testing operations may be electrospun for storage and used in conjunction with a testing kit or system, where the electrospun fibers may be combined with water and a sample to accomplish the desired assay or test.

With the preceding in mind, the present approach was implemented in a series of studies. In one study an aqueous solution including Ficoll® PM400, a protein stabilizing factor, was electrospun into a nanoscale fiber 50 with uniform structure and dimensions. Though the electrospinning of Ficoll® PM400 in solution is described in this example, other protein stabilizing factors and/or proteins (or other molecules of interest, as described herein) may also be incorporated into such a nanoscale fiber 50, providing a new storage medium that suitable for room temperature storage.

In the present example, an aqueous solution of 70% Ficoll® PM400 was prepared and subjected to an electrospinning process such as that disclosed in FIG. 1. The process was repeated using different electrospinning configuration parameters, as shown in Table 1:

TABLE 1

| | Receiving Distance | Voltage | Flow Rate |
|---|---|---|---|
| 1 | 15 cm | 18 kV | 0.15 ml/h |
| 2 | 25 cm | 25 kV | 0.25 ml/h |
| 3 | 35 cm | 18 kV | 0.25 ml/h | where receiving distance corresponds to the distance between the tip 18 and collector 24, voltage corresponds to the voltage applied by DC power source 22, and flow rate corresponds to the rate at which polymer solution 12 is expelled from the syringe 16 through tip 18.

Using the above settings and an aqueous solution of 70% Ficoll® PM400 as the polymer solution 12, nanoscale fibers 50 were generated and collected. Turning to FIGS. 2-4, the collected fibers 50 were imaged at two different magnifications using a scanning electron microscope. FIG. 2 shows images of the fiber 50 generated using the settings shown in row 1 of Table 1. FIG. 3 shows images of the fiber 50 generated using the settings shown in row 2 of Table 1. FIG. 4 shows images of the fiber 50 generated using the settings shown in row 3 of Table 1. As evidenced by the figures, the resulting fibers 50 of Ficoll® PM400 are less than 5 μm in diameter.

In other studies, nanoscale fibers were formed using a formulation of Ficoll® PM400, Ficoll® PM70, bovine serum albumin (BSA), and Taq polymerase. The nanoscale fibers formed from this formulation were found to retain their enzymatic activity after being stored at room temperature for 7 days.

Technical effects of the invention include electrospun fibers of biological compositions of interest, including enzymatic mixtures, antibody mixtures, nucleic acid mixtures, and so forth, as well as the production of such fibers. In certain embodiments, a technical effect may include the production of fiber coated substrates that may be sized for storage and/or use in a standardized reaction. Alternatively, in other embodiments, a technical effect may include the production of electrospun fibers not on (e.g., removed from) the collection substrate and provided for storage and/or use in a standardized reaction. The electrospun fibers generated as discussed herein are substantially uniform in diameter and dissolve in water very rapidly, e.g., in two seconds or less. The electrospun fibers discussed herein are not produced in a batch process but are instead produced in a continuous manner. Furthermore, the electrospun fibers discussed herein are not produced using a freeze drying process, such as a freeze drying batch process.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A biochemical storage medium, comprising: one or more continuously produced electrically spun fibers, wherein the one or more fibers have a nanoscale to microscale diameter and comprise one or more biologically active components; and,
    wherein the fibers are formed with a polysucrose protein stabilization factor and deposited onto a continuously provided substrate with the biologically active components bound to the fibers.

2. The biochemical storage medium of claim 1, further comprising a supportive layer on which the one or more fibers are deposited.

3. The biochemical storage medium of claim 2, wherein the supportive layer comprises one or more of a hydrophobic material, a hydrophilic material, a nitrocellulose membrane, a cellulose membrane, a cellulose acetate membrane, a regenerated cellulose membrane, a nitrocellulose mixed ester membrane, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene membrane, a glass fiber substrate, or a combination of two or more of the above membranes or substrates.

4. The biochemical storage medium of claim 1, wherein the one or more fibers have diameters between about 10 nm and 2000 nm.

5. The biochemical storage medium of claim 1, wherein the one or more fibers are soluble in aqueous solutions.

6. The biochemical storage medium of claim 1, wherein the one or more biologically active components comprise one or more proteins.

7. The biochemical storage medium of claim 6, wherein the one or more proteins comprise an enzyme or an antibody that retain biological activity when the one or more fibers are dissolved.

8. The biochemical storage medium of claim 1, wherein the fibers comprise one or more additional carbohydrates, stabilizing factors, or nucleotides.

9. The biochemical storage medium of claim 8, wherein the carbohydrates comprise one or more of polysucrose, melezitose, sucrose, trehalose, or sorbitol.

10. The biochemical storage medium of claim 8, wherein the stabilizing factors comprise one or more of albumin, polyethylene glycol, or polyvinyl alcohol.

11. The biochemical storage medium of claim 1, wherein the one or more biologically active components comprise one or more of labile small molecules, dNTP's, rNTP's, detergents, salts, divalent cations, buffer molecules, primers, flavin adenine dinucleotide (FAD), nicotinamide adenine dinucleotide (NAD), dye conjugated esters, or labeled molecules.

12. The biochemical storage medium of claim 1, wherein the one or more fibers are stable at room temperature for at least a week.

13. The biochemical storage medium of claim 1, wherein the fibers correspond to a quantity of the one or more biologically active components suitable for use in a preconfigured reaction.

14. A method of stabilizing a biologically active composition, comprising:
    Feeding in a continuous fashion a solution comprising one or more biologically active components of interest and a polysucrose protein stabilization factor to an extrusion component;
    Expelling in a continuous fashion the solution from the extrusion component;
    applying an electrostatic charge to the continuously expelled solution while applying an opposing charge to a continuously provided collector surface;
    and collecting one or more fibers with the biologically active components bound to the fibers continuously formed from the expelled and charged solution on the collector surface in a continuous process, wherein the fibers have diameters measuring in nanometers to micrometers.

15. The method of claim 14, wherein the solution is an aqueous solution.

16. The method of claim 14, wherein the collector surface comprises a substrate comprising one or more of a hydrophobic material, a hydrophilic material, a nitrocellulose membrane, a cellulose membrane, a cellulose acetate membrane, a regenerated cellulose membrane, a nitrocellulose mixed ester membrane, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene membrane, a glass fiber substrate, or a combination of two or more of the above membranes or substrates.

17. The method of claim 16, comprising:
processing the substrate with the collected fibers deposited thereon to form smaller pieces of the substrate with the collected fibers.

18. The method of claim 17, comprising:
storing the pieces of the substrate at room temperature for later use.

19. A method of using a stabilized biochemically active constituent, comprising:
selecting a quantity of an electrospun fiber produced according to claim 14, wherein the electrospun fibers have diameters between about 10 nm and about 2000 nm and wherein the fibers comprise the stabilized biologically active constituent;
adding the fibers to an aqueous environment, wherein the fibers dissolve in the aqueous environment to form an aqueous solution; and
using the aqueous solution in a biochemical reaction in which the stabilized biologically active constituent takes part in the biochemical reaction.

20. The method of claim 19, wherein the stabilized biochemically active constituent is a polymerase and the biological reaction is a nucleic acid amplification reaction.

21. The method of claim 19, wherein the stabilized biologically active constituent is an antibody and the biochemical reaction is an immunological reaction.

22. The method of claim 19, comprising:
storing the fiber-coated paper substrate prior to use at room temperature for at least a week.

23. A biochemical storage medium, comprising:
one or more continuously produced electrospun fibers deposited onto a continuously provided substrate;
wherein the one or more fibers further comprise one or more biologically active components;
wherein the one or more fibers further comprise bovine serum albumin and Taq polymerase; and,
wherein the one or more fibers further comprise polysucrose protein stabilization factors of at least two different molecular weights.

* * * * *